(12) United States Patent
Oubel et al.

(10) Patent No.: US 12,357,232 B2
(45) Date of Patent: Jul. 15, 2025

(54) METHOD FOR PREDICTING THE RECURRENCE OF A LESION BY IMAGE ANALYSIS

(71) Applicant: Quantum Surgical, Montpellier (FR)

(72) Inventors: Estanislao Oubel, Montpellier (FR); Lucien Blondel, Montpellier (FR); Bertin Nahum, Castelnau-le-Lez (FR); Fernand Badano, Lyons (FR)

(73) Assignee: Quantum Surgical, Montpellier (FR)

( * ) Notice: Subject to any disclaimer, the term of this patent is extended or adjusted under 35 U.S.C. 154(b) by 427 days.

(21) Appl. No.: 17/925,752

(22) PCT Filed: May 20, 2021

(86) PCT No.: PCT/FR2021/050906
§ 371 (c)(1),
(2) Date: Nov. 16, 2022

(87) PCT Pub. No.: WO2021/234304
PCT Pub. Date: Nov. 25, 2021

(65) Prior Publication Data
US 2023/0172535 A1    Jun. 8, 2023

(30) Foreign Application Priority Data
May 20, 2020   (FR) ...................... 2005338

(51) Int. Cl.
*G06T 7/11*      (2017.01)
*A61B 5/00*      (2006.01)
*G06T 7/00*      (2017.01)

(52) U.S. Cl.
CPC .......... *A61B 5/4848* (2013.01); *G06T 7/0016* (2013.01); *G06T 7/11* (2017.01);
(Continued)

(58) Field of Classification Search
CPC ....... A61B 5/4848; G06T 7/0016; G06T 7/11; G06T 2207/10028; G06T 2207/20081;
(Continued)

(56) References Cited

U.S. PATENT DOCUMENTS 12,211,151 B1 *   1/2025   Chiou ................... G06T 19/003
12,220,195 B2 *   2/2025   Junio ...................... A61B 34/70
(Continued)

FOREIGN PATENT DOCUMENTS

CN          101689220 A       3/2010
CN          105828709 A       8/2016
(Continued)

OTHER PUBLICATIONS

Kwon et al. PORTR Pre-Operative and Post-Recurrence Brain Tumor Registration, IEEE Transactions on Medical Imaging, vol. 33, No. 3, Mar. 2014 (Year: 2014).*
(Continued)

*Primary Examiner* — Ming Y Hon
(74) *Attorney, Agent, or Firm* — ArentFox Schiff LLP (57) ABSTRACT

The invention relates to a method for evaluating in post-treatment an ablation of a portion of an anatomy of interest of an individual, the anatomy of interest comprising at least one lesion. The post-treatment evaluation method comprises in particular a step of automatically evaluating a risk of recurrence of the lesion of the anatomy of interest of the individual based on the analysis of a pair of pre-operative and post-operative medical images of the anatomy of interest of the individual by means of automatic learning method of the neural network type, said method being preloaded during a so-called training phase on a database comprising a plurality of pairs of medical images of an anatomy of interest identical to a plurality of individuals, each medical image pair of the database being associated with a recur-
(Continued)

rence status of a lesion of the anatomy of interest of said patient. The invention also relates to an electronic device comprising a processor and a computer memory storing instructions of such an evaluation method.

15 Claims, 5 Drawing Sheets

(52) U.S. Cl.
CPC .............. *G06T 2207/10028* (2013.01); *G06T 2207/20081* (2013.01); *G06T 2207/20084* (2013.01); *G06T 2207/20132* (2013.01); *G06T 2207/30096* (2013.01)

(58) Field of Classification Search
CPC . G06T 2207/20084; G06T 2207/20132; G06T 2207/30096; G16H 30/40
See application file for complete search history.

(56) References Cited

U.S. PATENT DOCUMENTS

| | | | | |
|---|---|---|---|---|
| 2012/0230568 | A1* | 9/2012 | Grbic | G06V 10/803 382/128 |
| 2015/0369808 | A1* | 12/2015 | Freire Salinas | G01N 33/57415 435/6.12 |
| 2020/0410683 | A1* | 12/2020 | Hu | G06T 7/0016 |
| 2021/0145518 | A1* | 5/2021 | Mosnier | G06N 3/047 |
| 2021/0210195 | A1* | 7/2021 | Dogdas | G16H 30/40 |
| 2021/0233659 | A1* | 7/2021 | Chennubhotla | G06V 10/50 |
| 2021/0272694 | A1* | 9/2021 | Madabhushi | G06N 3/045 |
| 2022/0058801 | A1* | 2/2022 | Klimov | G06T 7/0012 |
| 2024/0115320 | A1* | 4/2024 | Chaitanya | A61B 18/18 |
| 2024/0331135 | A1* | 10/2024 | Long | G06T 3/40 |
| 2024/0341960 | A1* | 10/2024 | Casey | G16H 30/40 |
| 2025/0049972 | A1* | 2/2025 | Donovan | A61K 51/088 |

FOREIGN PATENT DOCUMENTS

| | | |
|---|---|---|
| CN | 106408610 A | 2/2017 |
| CN | 107049475 A | 8/2017 |
| CN | 107208132 A | 9/2017 |
| CN | 107624192 A | 1/2018 |
| CN | 108922602 A | 11/2018 |
| CN | 109859833 A | 6/2019 |
| CN | 109996508 A | 7/2019 |
| CN | 110111892 A | 8/2019 |
| CN | 110189824 A | 8/2019 |
| CN | 110198680 A | 9/2019 |
| CN | 110251122 A | 9/2019 |
| CN | 110782474 A | 2/2020 |
| CN | 111128328 A | 5/2020 |
| JP | 2019-033960 A | 3/2019 |
| JP | 2019-536536 A | 12/2019 |
| WO | 2020/008834 A1 | 1/2020 |

OTHER PUBLICATIONS

Wang et al., "Detection and Monitoring of Microwave Ablation by Ultrasound Imaging Based on Convolutional Neural Network," 2020 IEEE International Ultrasonics Symposium, 2020, 3 pages.
Egger et al, "Interactive Volumetry of Liver Ablation Zones", vol. 5, No. 1, Oct. 20, 2015, Scientific Reports, Retrieved from the Internet: www.nature.com/articles/srep15373.
Zhang et al, "Detection and Monitoring of Thermal Lesions Induced by Microwave Ablation Using Ultrasound Imaging and Convolutional Neural Networks", Sep. 5, 2019, vol. 24, No. 4, p. 965-973.
International Search Report and Written Opinion mailed, Aug. 13, 2021, for PCT/FR2021/050906.

* cited by examiner

METHOD FOR PREDICTING THE RECURRENCE OF A LESION BY IMAGE ANALYSIS

CROSS-REFERENCE TO RELATED APPLICATIONS:

This application is a National Phase of PCT/FR2021/050906, filed on May 20, 2021, which claims priority to FR Patent Application No. 2005338, filed on May 20, 2020, the disclosures of which are hereby incorporated by reference in their entireties.

TECHNICAL FIELD OF THE INVENTION

The field of the invention is that of evaluating a medical intervention.

The invention relates more specifically to a method for the post-treatment evaluation of a risk of recurrence of an ablated lesion.

The invention is applicable in particular for evaluating a minimally invasive medical intervention by predicting a risk of recurrence of a lesion, such as a tumor or a metastasis. Such a minimally invasive medical intervention corresponds for example to a percutaneous ablation of a lesion, for example a tumor in the liver, a lung, a kidney or any other organ. A percutaneous ablation generally consists in using images to guide the insertion of one or more needles through the skin so as to reach and destroy a lesion.

DESCRIPTION OF THE PRIOR ART

The prior art discloses techniques for evaluating the effectiveness of an intervention and for predicting a risk of recurrence of a lesion.

Such a technique consists for example, following the ablation of a lesion, in determining the extent to which the ablation region covers the lesion. By comparing the volume of the ablation region with the volume of the lesion, it is possible to determine the ablation margins. In practice, it is generally recommended to have ablation margins of at least five millimeters.

In order to determine these margins, the volume of the lesion is generally determined when planning the intervention and compared with the volume of the ablation region, which is segmented by an operator on at least one post-operative image.

The major drawback is that the volume of the ablation region is generally determined inaccurately, often in a manner depending on the operator who performed the segmentation. In addition, the quality of post-operative images is often poor, thereby contributing to introducing uncertainties in the segmentation. A correlation between ablation margins and a risk of recurrence of a lesion is therefore difficult to establish.

In order to improve the techniques from the prior art, it is known to use methods for automatically segmenting the ablation region.

Such a technique is described for example in the scientific publication by Zhang et al, entitled "Detection and Monitoring of Thermal Lesions Induced by Microwave Ablation Using Ultrasound Imaging and Convolutional Neural Networks", published in September 2019. The segmentation method described in this publication makes it possible to calculate the margins of the ablation region by segmenting a pre-operative ultrasound image and a post-operative ultrasound image.

However, the segmentation method described in this publication does not make it possible to predict the risk of recurrence, since the accuracy of the automatic segmentation of the ablation region is low. Firstly, the segmentation method is limited to a sub-sampling matrix of an image of the ablation region, the size of which is fixed, generally equal to 4 $mm^2$, thus limiting the use of the method to regions of small dimensions. In addition, it is necessary to know the position of the ablation region in order to set the position of the sub-sampling matrix, making the method difficult to use in the absence of constant reference points inside the sub-sampling matrix in the pre-operative and post-operative images. Finally, due to the nature and the quality of two-dimensional ultrasound images, the anatomy of interest may be difficult to ascertain, making segmentation of the region inaccurate, resulting in particular in incorrect observations in which the ablation region, as segmented, does not encompass the lesion to be ablated.

In addition, automatic segmentation methods give consistent results for homogeneous regions, that is to say for example for a bone, blood vessels, or a lesion, or when the image contains a known number of regions. In the case of an ablation region, the segmentation results that are obtained are inconsistent since ablation regions are very complex regions generally consisting of various materials such as gas, necrosed cells, healthy cells, residual contrast product, calcification, etc. Moreover, segmentation is generally performed on medical images that are generally blurry and of poor contrast, making it difficult to automatically segment the image.

None of the current systems make it possible to simultaneously meet all the required needs, specifically to provide a technique that makes it possible to finely evaluate a risk of recurrence of a previously ablated lesion, in particular based on an unclear and/or poor-contrast medical image, without requiring the intervention of an experienced operator.

SUMMARY OF THE INVENTION

The present invention aims to rectify all or some of the abovementioned drawbacks of the prior art.

To this end, the invention targets a method for the post-treatment evaluation of an ablation of part of an anatomy of interest of an individual, the anatomy of interest comprising at least one lesion, the ablated part of the anatomy of interest being called an ablation region.

The ablation is percutaneous or minimally invasive, this generally consisting in inserting at least one needle through the skin so as to reach and destroy a lesion. Multiple ablation techniques are possible: radiofrequency, microwave, electroporation, laser, cryotherapy, ultrasound, etc.

The anatomy of interest may be a liver, a lung, a kidney, or any other organ susceptible to lesions.

According to the invention, the post-treatment evaluation method comprises steps of:
  acquiring a post-operative medical image of the anatomy of interest of the individual;
  readjusting the post-operative image and a medical image of the anatomy of interest of the individual, acquired before the surgical treatment, called a pre-operative medical image, the readjusted pre-operative medical image and the readjusted post-operative medical image forming a pair of medical images of the anatomy of interest of the individual;
  evaluating a risk of recurrence of the lesion of the anatomy of interest of the individual using a neural network-based machine learning method, analyzing the pair of medical images of the anatomy of interest of the individual, said machine learning method being trained beforehand in what is called a training phase on a database containing a plurality of pairs of medical images of an identical anatomy of interest of a set of patients, each pair of medical images in the database being associated with a recurrence status of a lesion of the anatomy of interest of said patient.

A risk of recurrence of a lesion is thus predicted based on previous clinical data by performing very large-scale analysis of pairs of medical images of a given anatomy, for example a liver when the anatomy of interest to be treated is a liver. This analysis makes it possible to ascertain a more precise estimate of the risk of recurrence of the lesion to be ablated, without requiring the presence of an experienced operator. The post-treatment evaluation method according to the invention thus offers medical staff a better view of the treatment applied to the individual, by allowing them to assess the need for additional treatment if the risk of recurrence turns out to be significant.

The recurrence status generally takes either what is called a positive value when a recurrence has been observed or what is called a negative value where no recurrence has been observed on a post-operative check-up date.

The risk of recurrence for its part generally takes the form of a probability of between 0 and 1.

Advantageously, the risk of recurrence is evaluated at a predetermined date following the treatment, each pair of medical images in the database also being associated with a date of recurrence when the recurrence status is positive.

The date may be for example 1 month, 3 months, 6 months, 1 year, 2 years, 5 years, or even 10 years following the ablation treatment.

The term pre-operative medical image is understood to mean a medical image acquired before the ablation treatment, and the term post-operative medical image is understood to mean a medical image acquired after the ablation treatment.

In some particular modes of implementation of the invention, all or some of the pairs of training images in the database are cropped, after readjustment, around the ablation region comprising at least one lesion, the images being cropped within a common frame of predetermined size, the set of centers of the ablation region in the cropped pairs of images forming a constellation of distinct points within the common frame.

Thus, by distributing the position of the ablation regions within the common frame, it is possible to reduce prediction errors of the machine learning method. If all of the ablation regions were to be in the same position in the common frame, the machine learning method would mainly consider the pairs of images having an ablation region in this particular position, thus leading to prediction errors if the ablation region were to be in another position.

In some particular modes of implementation of the invention, for all of the previously cropped pairs of medical images in the database, the part of the body of the individual contained in the image is divided into a plurality of elementary units of a single size, the number of elementary units being split into two almost equal portions between the part of the human body delimited by the ablation region and the rest of the part of the body of the individual contained in the image.

In other words, the number of elementary units is split into two almost equal portions between the part of the human body delimited by the ablation region and the rest of the part of the body of the individual contained in the pairs of cropped images in the database.

It should be emphasized that the equivalent distribution between the elementary units corresponding to an ablation region and the elementary units corresponding to a non-ablation region may be analyzed at the level of an image or globally at the level of all of the images.

The elementary units are generally called pixels in the context of two-dimensional images or voxels in the context of three-dimensional images.

Almost equal portions will be understood to mean when the two sets of elementary units consist of the same number of elementary units or when the difference in the number of elementary units in each of the two sets is for example less than 5% of the number of elementary units in the two sets.

In some particular modes of implementation of the invention, the database of pairs of medical images contains at least one pair of images without an ablation region.

The machine learning method is thus optimally trained by having at least one pair of images where no ablation has been performed.

In some particular modes of implementation of the invention, the post-treatment evaluation method also comprises a step of determining an additional ablation mask when the risk of recurrence is greater than a predetermined threshold value.

A treatment proposal is thus estimated in order to improve the risk of recurrence using the post-treatment evaluation method. It should be emphasized that this additional treatment proposal is non-binding and may or may not be followed by medical staff.

It should be emphasized that the additional ablation mask is a display of the region to be ablated during the additional treatment. The ablation mask is generally generated when the risk of recurrence is greater than a threshold value, for example 0.5, after having:

detected and segmented the lesion and the ablation region in the pre-operative image and in the post-operative image, respectively;
  determined at least one position of the recurrence.

The detection and the segmentation may furthermore have been performed automatically or manually by an operator.

In some particular modes of implementation of the invention, the step of determining an additional ablation mask comprises a sub-step of segmenting the ablation region in the post-operative image of the anatomy of interest of the individual.

The segmentation may be performed automatically or manually by an operator. It should be emphasized that the ablation region has generally been detected beforehand in the image, where at least one operator has indicated its position in the image.

In some particular modes of implementation of the invention, the step of determining an additional ablation mask comprises a sub-step of detecting the ablation region in the post-operative image of the anatomy of interest of the individual.

In some particular modes of implementation of the invention, the step of determining an additional ablation mask comprises a sub-step of detecting the lesion in the pre-operative image of the anatomy of interest of the individual.

The segmentation may thus be performed around the lesion detected in the medical image.

In some particular modes of implementation of the invention, the step of determining an additional ablation mask comprises a sub-step of determining the position of the recurrence as a function of at least one risk predictor chosen from the list comprising:
- an ablation margin between the ablation region and the lesion,
- a distance between a center of mass of the lesion and a center of mass of the ablation region,
- the regularity and sharpness of the edges of the ablation region with respect to the surrounding healthy tissue,
- the ratio between the volume of the lesion and the volume of the ablation region,
- a position of the lesion with respect to the center of the anatomy of interest.

In some particular modes of implementation of the invention, the medical images are three-dimensional images.

It should be emphasized that a three-dimensional image may for example correspond to a collection of two-dimensional images taken at generally regular intervals along a predefined axis.

In some particular modes of implementation of the invention, each pre-operative image is acquired using a first image acquisition technique and each post-operative image is acquired using a second image acquisition technique, the first technique and the second technique being identical or different.

In some particular modes of implementation of the invention, the post-treatment evaluation method also comprises a step of proposing a trajectory of a medical instrument to a target point of an ablation region defined by the additional ablation mask.

It should be emphasized that this step of proposing a trajectory, which may also be called a step of planning a trajectory, is performed prior to the additional treatment, and in particular to any medical action on the individual. It should also be emphasized that this trajectory is non-binding and may or may not be followed by medical staff.

In some particular modes of implementation of the invention, the post-treatment evaluation method also comprises a step of helping an operator to follow the planned trajectory of the medical instrument.

In some particular modes of implementation of the invention, the planned trajectory and/or a guidance indication is displayed in real time on a screen of an augmented reality device.

The invention also relates to an electronic device comprising a processor and a computer memory storing instructions of a method according to any one of the above modes of implementation.

Such an electronic device may be for example a control device, a navigation system, a robotic device or an augmented reality device. The control device may in particular be a computer present in the operating theater, or a remote server.

In other words, the invention relates to an electronic device comprising a processor and a computer memory storing instructions of a method for the post-treatment evaluation of an ablation of part of an anatomy of interest of an individual, the anatomy of interest comprising at least one lesion, the ablated part of the anatomy of interest being called an ablation region, the processor being configured, when executing the instructions, so as to:
- acquire a post-operative medical image of the anatomy of interest of the individual, comprising all or part of the ablation region;
- readjust the post-operative image and a medical image of the anatomy of interest of the individual, acquired before the surgical treatment, called a pre-operative medical image, the readjusted pre-operative medical image and the readjusted post-operative medical image forming a pair of medical images of the anatomy of interest of the individual;
- evaluate a risk of recurrence of the lesion of the anatomy of interest of the individual using a neural network-based machine learning method, analyzing the pair of medical images of the anatomy of interest of the individual, said machine learning method being trained beforehand in what is called a training phase on a database containing a plurality of pairs of medical images of an identical anatomy of interest of a set of patients, each pair of medical images in the database being associated with a recurrence status of a lesion of the anatomy of interest of said patient.

In some particular embodiments of the invention, the processor is configured so as to evaluate the risk of recurrence at a predetermined date following the treatment, each pair of medical images in the database also being associated with a date of recurrence when the recurrence status is positive.

In some particular embodiments of the invention, the processor is furthermore configured, after the readjustment, so as to crop all or some of the pairs of images in the database, around an ablation region contained in the post-operative image of all or some of the pairs of training images, the images being cropped within a common frame of predetermined size, the set of centers of the ablation region in the cropped pairs of images forming a constellation of distinct points within the common frame.

In some particular embodiments of the invention, for all of the previously cropped pairs of medical images in the database, the processor is furthermore configured so as to divide the part of the body of the individual contained in the image into a plurality of elementary units of a single size, the number of elementary units being split into two almost equal portions between the part of the human body delimited by the ablation region and the rest of the part of the body of the individual contained in the image.

In some particular embodiments of the invention, the database of pairs of medical images contains at least one pair of images without an ablation region.

In some particular embodiments of the invention, the processor is furthermore configured so as to determine an additional ablation mask when the risk of recurrence is greater than a predetermined threshold value.

In some particular embodiments of the invention, the processor is furthermore configured so as to detect the ablation region in the post-operative image of the anatomy of interest of the individual when determining an additional ablation mask.

In some particular embodiments of the invention, the processor is furthermore configured so as to segment the ablation region in the post-operative image of the anatomy of interest of the individual when determining an additional ablation mask.

In some particular embodiments of the invention, the processor is furthermore configured so as to detect the lesion in the pre-operative image of the anatomy of interest of the individual when determining an additional ablation mask.

In some particular embodiments of the invention, the processor is furthermore configured so as to segment the lesion in the pre-operative image of the anatomy of interest of the individual when determining an additional ablation mask.

In some particular embodiments of the invention, when determining an additional ablation mask, the processor is furthermore configured so as to determine the position of the recurrence as a function of at least one risk predictor chosen from the list comprising:

an ablation margin between the ablation region and the lesion, a distance between a center of mass of the lesion and a center of mass of the ablation region, the regularity and sharpness of the edges of the ablation region with respect to the surrounding healthy tissue, the ratio between the volume of the lesion and the volume of the ablation region, a position of the lesion with respect to the center of the anatomy of interest.

In some particular embodiments of the invention, the medical images are three-dimensional images.

In some particular embodiments of the invention, each pre-operative image is acquired using a first image acquisition technique and each post-operative image is acquired using a second image acquisition technique, the first technique and the second technique being identical or different.

BRIEF DESCRIPTION OF THE FIGURES

Other advantages, aims and particular features of the present invention will become apparent from the following non-limiting description of at least one particular embodiment of the devices and methods that form the subject of the present invention, with reference to the appended drawings, in which.

DETAILED DESCRIPTION OF THE INVENTION

The present description is given without limitation, each feature of one embodiment being able to be combined with any other feature of any other embodiment in an advantageous manner.

It will be noted, from now on, that the figures are not to scale.

Example of One Particular Mode of Implementation

Figure 1:
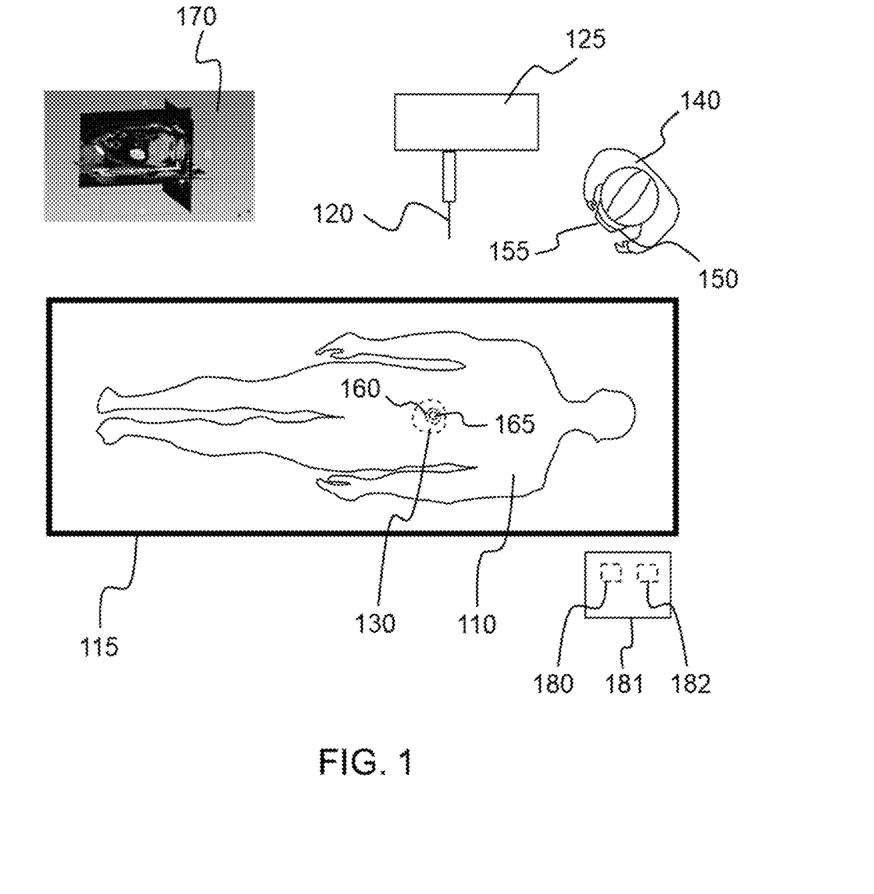
FIG. 1 is a schematic view of a medical intervention.

FIG. 1 is a schematic view of a medical intervention in which an individual 110 lying on a table 115 is being treated with a medical instrument 120. In the present non-limiting example of the invention, the medical intervention corresponds to the ablation of a lesion 165 in an anatomy of interest 130, which is in this case the liver of the individual 110, by way of the medical instrument 120, which is in this case a semi-rigid needle. The medical intervention is in this case a percutaneous procedure during which the body of the individual 110 is not opened up.

The handling of the medical instrument 120 by an operator 140 may advantageously be guided by way of a guidance device which, in the present non-limiting example of the invention, is an augmented reality device, such as a headset 150 worn by the operator 140. The medical instrument 120 may also be associated with a robotic medical device 125.

The headset 150 comprises a translucent screen 155 allowing the operator to see normally. An image is displayed on the screen 155 in overlaid form so as to display markers that make it possible to guide the operator 140 in the handling of the medical instrument 120 with a view to treating, through ablation, a region 160, called an ablation region, around the lesion 165 identified in the anatomy of interest 130. The markers may in particular comprise an ablation mask that has been estimated beforehand on a medical image 170 of the anatomy of interest 130 acquired before the operation. The medical image 170 will be called a pre-operative medical image 170 hereinafter.

Figure 2:
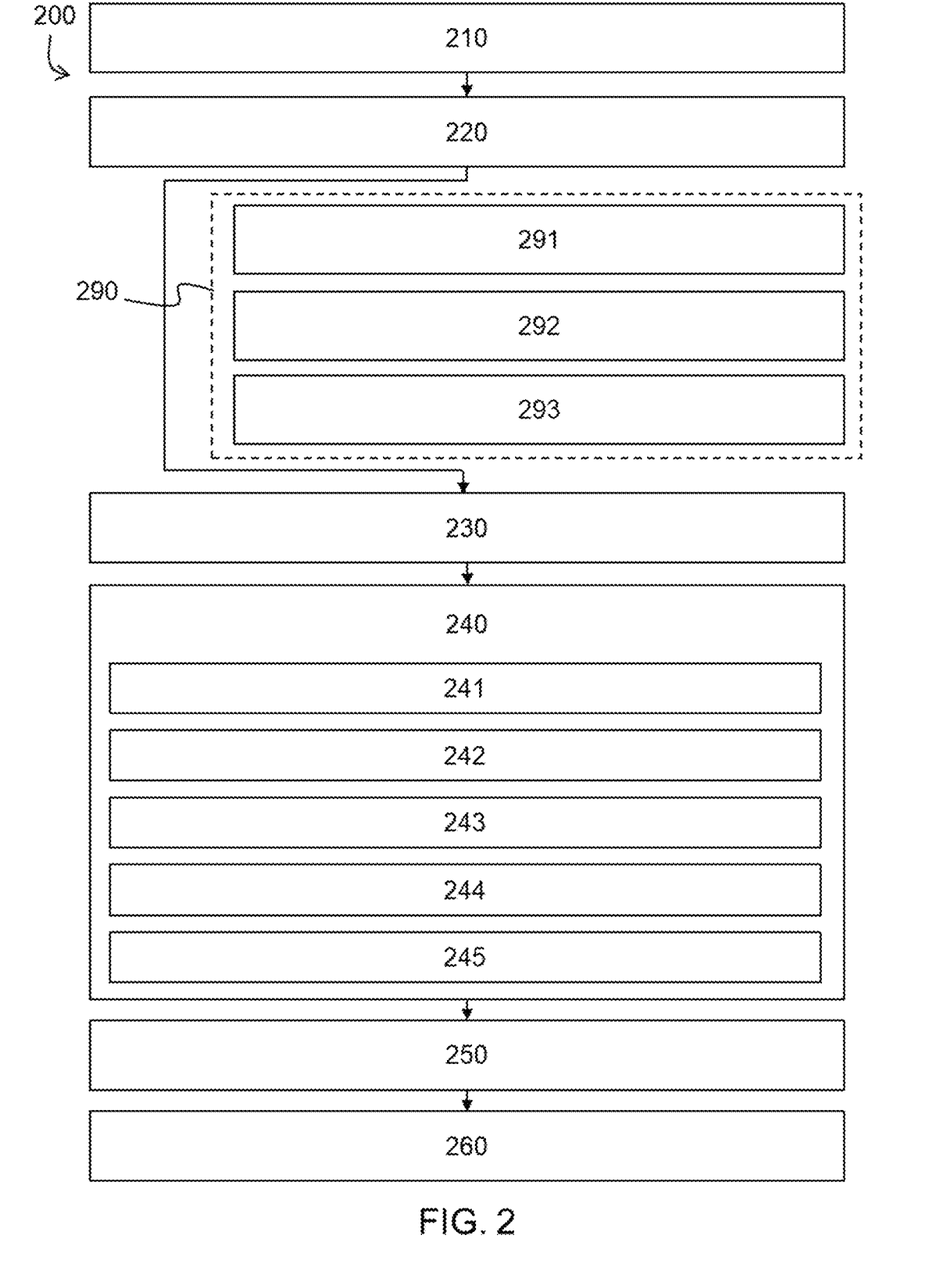
FIG. 2 is an overview of a method for the post-treatment evaluation of the medical intervention from FIG. 1.

When the operation is complete, the operative treatment is evaluated using a method 200 for the post-treatment evaluation of the ablation, as illustrated in the overview of FIG. 2, and the instructions of which are stored in a computer memory 180 of an electronic control device 181 connected to the headset 155 by a cable or through wireless technology. The post-treatment evaluation method 200, the instructions of which are processed by a computer processor 182 of the electronic control device 181, makes it possible in particular to determine a risk of recurrence associated with the lesion, in order to verify whether the surgical treatment performed during the operation is sufficient or whether it is preferable to continue the treatment, for example by performing an additional ablation.

It should be emphasized that the electronic device 181 may advantageously be integrated into the headset 150.

The post-treatment evaluation method 200 comprises a first step 210 of acquiring a post-operative medical image of the anatomy of interest 130.

It should be emphasized that the pre-operative and post-operative medical images are preferably acquired using computed tomography. As an alternative, they may be acquired using a magnetic resonance imaging apparatus.

The technique used to acquire the pre-operative medical image and the post-operative medical image are preferably similar, or even identical.

In other words, the technique used to acquire the pre-operative and post-operative medical images is advantageously identical to that used to acquire the medical images in the training database of the machine learning method.

However, the technique used to acquire the post-operative medical image may be different from the technique used to acquire the pre-operative medical image.

In this case, the techniques used to acquire the pre-operative and post-operative medical images are advantageously identical to those used to acquire the medical images in the training database of the machine learning method.

The pre-operative and post-operative medical images are advantageously images acquired in three dimensions in the present non-limiting example of the invention. In practice, each medical image acquired in three dimensions generally corresponds to a collection of two-dimensional medical images each corresponding to a section of the anatomy of interest 130, taken at regular intervals along a predetermined axis. A three-dimensional representation of the anatomy of interest may be reconstructed from this collection of two-dimensional medical images. The term three-dimensional image will thus be understood to mean both a collection of medical images and a three-dimensional representation. The term voxel will be understood to mean an elementary unit in relation to the resolution of the three-dimensional image.

As an alternative, the pre-operative and post-operative medical images are each acquired in two dimensions. The elementary unit in relation to the resolution of the two-dimensional image is then commonly called a pixel.

The pre-operative and post-operative medical images are images containing the entire anatomy of interest or that are cropped around the ablation region within a predefined frame. In a three-dimensional image, the frame surrounding the ablation region corresponds to a cube. In a two-dimensional image, on the other hand, the frame corresponds to a square.

The frame surrounding the ablation region, also known as "bounding box", may be generated automatically around the ablation region following an action by the operator. Such an action may for example correspond to the fact that the operator indicates a point in the post-operative medical image belonging to the ablation region, and the frame is generated around this point. By way of example, in the context of a minimally invasive ablation treatment on small lesions, that is to say for example on lesions of the order of 5 cm ±/− 10% maximum diameter, or even preferably of the order of 3 cm ±/− 10% maximum diameter, each edge of the cube or each side of the square measures between 5 and 10 cm.

Figure 3:
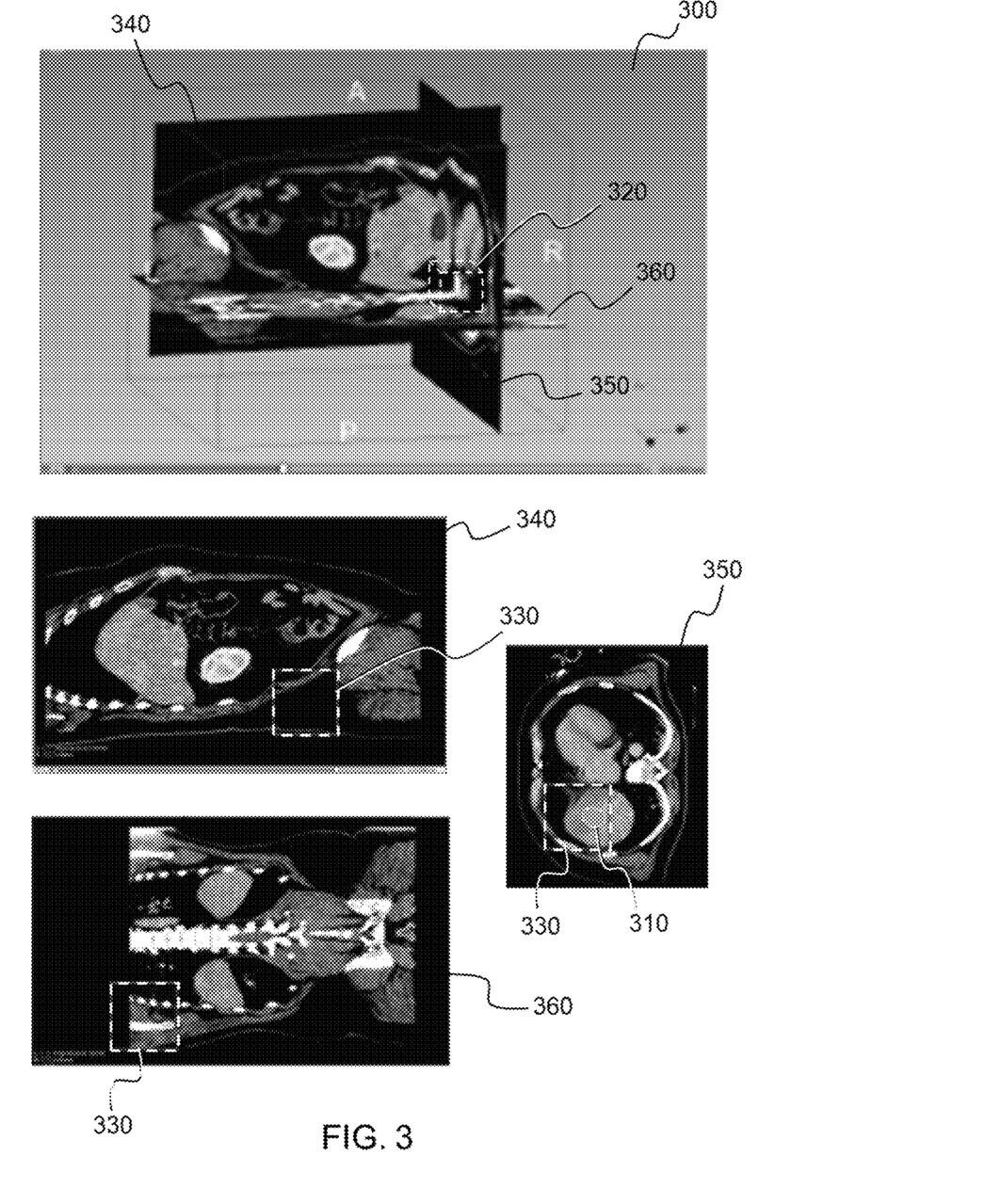
FIG. 3 is an example of a three-dimensional medical image in which an ablation region is highlighted, this image being used in the method illustrated in FIG. 2.

FIG. 3 is an illustration of a three-dimensional medical image 300 in which an ablation region 310 is surrounded by a frame 320. The frame 320 is cubic and corresponds to squares 330 on the sectional views 340, 350 and 360, respectively along the sagittal view, along the axial view and along the coronal view.

The post-operative medical image is readjusted with the pre-operative medical image 170 in a second step 220 of the method 200 illustrated in FIG. 2. The readjustment for finding matches between anatomical points of the two medical images is performed using a method known to those skilled in the art. The readjustment may be performed rigidly, that is to say that all of the points in the images are transformed in the same way, or non-rigidly, that is to say that each point in the images may have a specific transformation.

The two readjusted pre-operative and post-operative images form a pair of medical images of the anatomy of interest 130 of the individual 110.

The pair of medical images of the anatomy of interest 130 is then analyzed by a neural network, which is a machine learning method, in a third step 230 in order to automatically evaluate a risk of recurrence associated with the ablation treatment.

To this end, the neural network has been trained beforehand on a database of pairs of medical images of an identical anatomy of interest, therefore a liver in this case, of a set of patients in a preliminary training phase 290. Each pair of medical images comprises a pre-operative image and a post-operative image of an anatomy of interest having a function identical to that of the anatomy of interest 130.

Advantageously, the pair of medical images of the anatomy of interest 130 of the individual 110 are acquired using the same technique as that for the medical images in the pairs in the training database of the neural network. In other words, the pre-operative medical images are acquired using a first medical imaging technique and the post-operative medical images are acquired using a second medical imaging technique that may be identical to or different from the first medical imaging technique. Using an identical technique, possibly with different parameters, for the same type of medical image, that is to say for the pre-operative medical images and/or for the post-operative medical images, makes it possible to improve the results obtained by the neural network by reducing the biases associated with separate medical imaging techniques.

When the medical images of the anatomy of interest 130 of the individual 110 are cropped, the dimensions of the cube or of the square of these medical images are advantageously identical to those of the cubes or squares used to train the neural network.

In order to train the neural network, each pair of medical images in the database is associated with a recurrence status of a lesion of the liver of the person, the status indicating whether or not a recurrence has occurred, possibly associated with the date of recurrence. It should be emphasized that each of these pairs of medical images generally originates from a different person.

The phase 290 of training the neural network is generally performed in several steps:
- a training step 291;
- a validation step 292;
- a test step 293.

The database of pairs of medical images is thus partitioned into three databases containing separate pairs of medical images. The three databases are called training base, validation base and test base, respectively. In the present non-limiting example of the invention, 60 to 98% of the pairs of medical images in the database of medical images are grouped into the training base, 1 to 20% are grouped into the validation base and 1 to 20% are grouped into the test base. The percentages, which are generally dependent of the number of images in the database of medical images, are given here by way of indication.

The first two steps 291 and 292 of the phase 290 of training the neural network are main steps that may be repeated several times. The third test step is optional, for its part.

In the first step 291 of the training phase 290, a weight W and a bias b for each neuron of the neural network are determined from the pairs of medical images in the training base.

It should be emphasized that the training base may advantageously contain pairs of images without an ablation region.

In addition, it may be preferable for the set of images in the database to contain as many voxels belonging to the ablation region as there are voxels belonging to a non-ablation region. This proportion is calculated based on the classification of the voxels as determined manually by operators.

In other words, for all of the cropped pairs of medical images in the database, the part of the body of the individual contained in the image is divided into a plurality of elementary units of a single size, the number of elementary units being split into two almost equal portions between the part of the human body delimited by the ablation region and the rest of the part of the body of the individual contained in the image.

Almost equal portions will be understood to mean when the two sets of elementary units consist of the same number of elementary units or when the difference in the number of elementary units in each of the two sets is for example less than 5% of the number of elementary units in the two sets.

Moreover, the position of the ablation region in some of the pairs of readjusted medical images may advantageously be shifted randomly with respect to the center of the image in a random manner, so as to avoid the introduction of a bias into the neural network, which would learn that the ablation region is mainly a region in the center of the frame. Specifically, there are some medical images that are framed incorrectly by the operator around the ablation region. A bounded random variable is therefore advantageously added to the position of the frames in order to limit this bias in positioning the lesion in the center of the frame.

The second step 292 of the training phase 290 makes it possible to validate the weight W and the bias b that are determined beforehand for each neuron of the neural network, from the pairs of medical images in the validation base, in order to verify the results of the neural network, in particular the prediction error, that is to say through comparison for each pair of medical images in the validation database, that is to say the risk of recurrence obtained using the neural network, with the recurrence status associated with the pair of medical images, respectively.

If the prediction error is too great at the end of this second step, the two training 291 and validation 292 steps are implemented again in order to retrain the neural network by reusing the same pairs of medical images, in order to refine the values of the weights W and the biases b of each neuron.

As an alternative, during the retraining of the neural network, the first step 291 uses resampling of the pairs of medical images by considering, for training, the pairs of medical images in the training database and some of the pairs of medical images in the validation base. The rest of the pairs of medical images in the validation base are then used to validate the weights W and the biases b obtained at the end of the first retraining step.

It should be emphasized that the neural network may be retrained as many times as necessary until the prediction error is acceptable, that is to say is less than a predetermined value.

When the two steps 291 and 292 of the training phase 290 are implemented at least once, the final performance of the neural network may be tested in a possible third test step 293 with the pairs of medical images in the test base. These pairs of medical images, which are separate from the pairs of medical images in the training and validation bases, make it possible to verify that the neural network, as configured with the parameters W and b for each neuron, makes it possible to accurately predict the risk of recurrence in all situations with which the neural network is liable to be confronted. However, unlike validation step 292, this possible third test step 293 does not result in a new training cycle for the neural network.

It should be emphasized that the images used in test step 293 are generally carefully selected in order to cover various positions and sizes of the ablation region in the anatomy of interest in order to optimally test the predictive capabilities of the neural network.

The prediction of a risk of recurrence associated with the surgical treatment is obtained directly by the neural network that has been trained beforehand on a database of pairs of medical images each associated with a recurrence status.

The associated recurrence status is for example equal to 0 when there has been no recurrence of the lesion within a given period following the ablation (negative status) or to 1 when there has been a recurrence of the lesion within a given period following the ablation (positive status). The period associated with the estimate of the recurrence status is preferably 6 months. However, it is possible to estimate the recurrence status at various dates following the ablation by associating a recurrence date when the recurrence status is positive. For example, the neural network may also be trained to predict the recurrence statuses associated with a pair of medical images every 6 months following the ablation or 1 month, 3 months, 6 months, 1 year, 2 years, 5 years or 10 years following the ablation.

The value of the risk of recurrence of the lesion generally takes the form of a probability between 0 and 1.

If the value of the risk of recurrence is greater than a predetermined threshold value, that is to say that the probability of a recurrence possibly occurring within a given period, additional treatment may be proposed by the post-treatment evaluation method 200 by estimating an additional ablation mask that is estimated in a fourth step 240 of the post-treatment evaluation method 200. This additional, non-binding treatment corresponds for example to an additional ablation in a region in which the ablation margin is less than a given value, for example five millimeters.

Step 240 of generating an additional ablation mask generally comprises five sub-steps, numbered 241 to 245 in FIG. 2.

In sub-step 241, the lesion 165 is detected in the pre-operative medical image of the anatomy of interest 130 of the individual 110. This detection may be performed automatically or manually by an operator.

In sub-step 242, an ablation mask is generated around at least one lesion of the anatomy of interest by a second neural network based on the learning of medical images from a second database. In this second database, the majority of the medical images contain an ablation region that is detected and segmented beforehand on a patient exhibiting a liver lesion.

Figure 4:
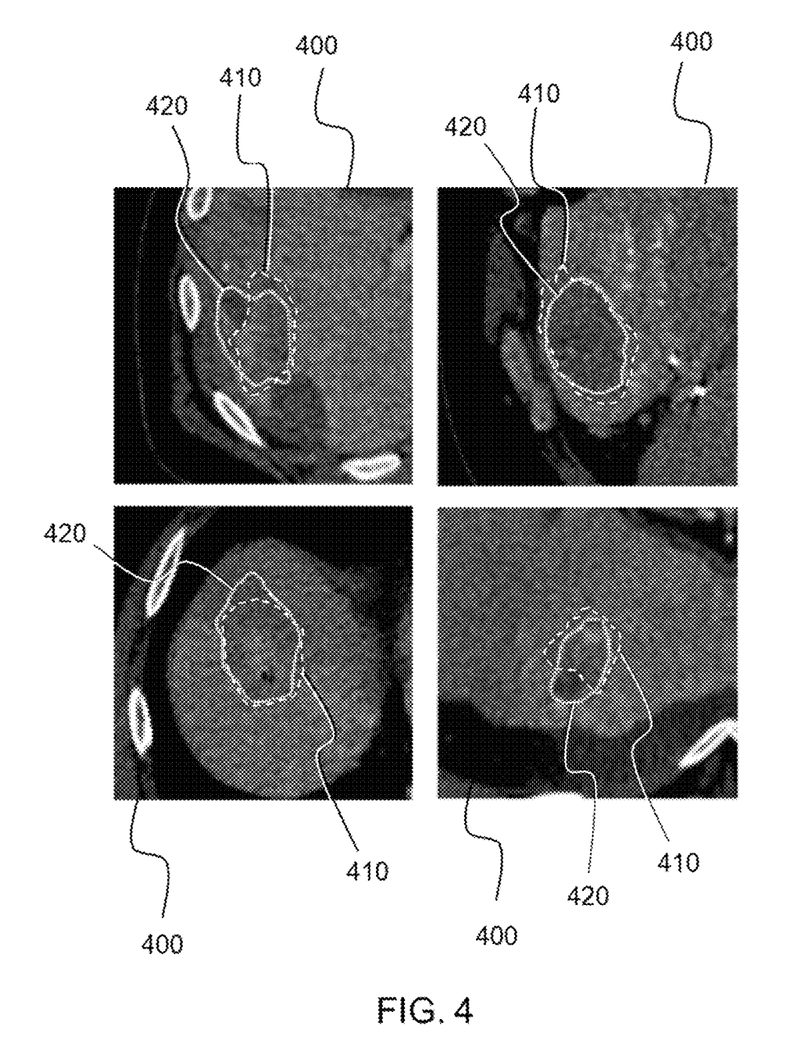
FIG. 4 is an example of four medical images each containing an ablation mask delimited manually by an operator and an ablation mask predicted by a neural network of the method illustrated in FIG. 2.

FIG. 4 illustrates four medical images 400 in this second database. Each medical image 400 has been annotated manually by an operator, who has delimited an ablation region 410. The neural network has generated an ablation mask 420.

It should be emphasized that, for each medical image in the second database, the ablation region has advantageously been determined manually by at least two operators, in order to increase the relevance of the training and therefore of the analysis results obtained by the second neural network. Specifically, it may be difficult for an operator to delimit an ablation region, in particular when the contrast in the image is poor, as in the images 400 in FIG. 4. Using several operators annotating the medical images therefore makes it possible to improve the identification of the ablation region. The ablation region associated with the pair of readjusted pre-operative and post-operative medical images thus corresponds, in the present non-limiting example of the invention, to the union of the ablation regions suggested by the operators. As an alternative example, the ablation region associated with a medical image may correspond to the intersection, to a consensus or to an adjudication of the ablation regions suggested by the operators. The neural network is furthermore trained to classify the voxels of a medical image into an ablation region or non-ablation region.

As an alternative, training may be performed using a single expert annotator delimiting ablation regions in medical images. The operator's experience is then important for the second neural network to be able to arrive at well-delimited ablation regions.

It should also be emphasized that the second database may have the same advantages as the first database in order to limit the training biases of the second neural network, specifically that it may contain images without an ablation region, that the positions of the ablation regions are not systematically at the center of the image and that the set of images in the database contains as many voxels in the ablation region as there are in the non-ablation region of the anatomy part visible in the image.

From the post-operative medical image of the anatomy of interest 130 of the individual, the second neural network classifies each voxel into an ablation region or non-ablation region. This prediction may take the form of an ablation mask superimposed on the pair of medical images of the anatomy of interest 130. The ablation mask is generally readjusted to the voxels belonging to the ablation region predicted by the second neural network. It should be emphasized that the ablation mask is generally delimited by an area or by a contour in the context of a two-dimensional image.

In sub-step 243, the lesion 165 is automatically segmented on the pre-operative medical image of the anatomy of interest 130 of the individual 110. As an alternative, the segmentation is performed manually by an operator.

The lesion is segmented automatically using methods known to those skilled in the art. For example, the segmentation is performed using a method based on the histogram of the image, such as for example the Otsu method, or using a deep learning method.

Figure 5:
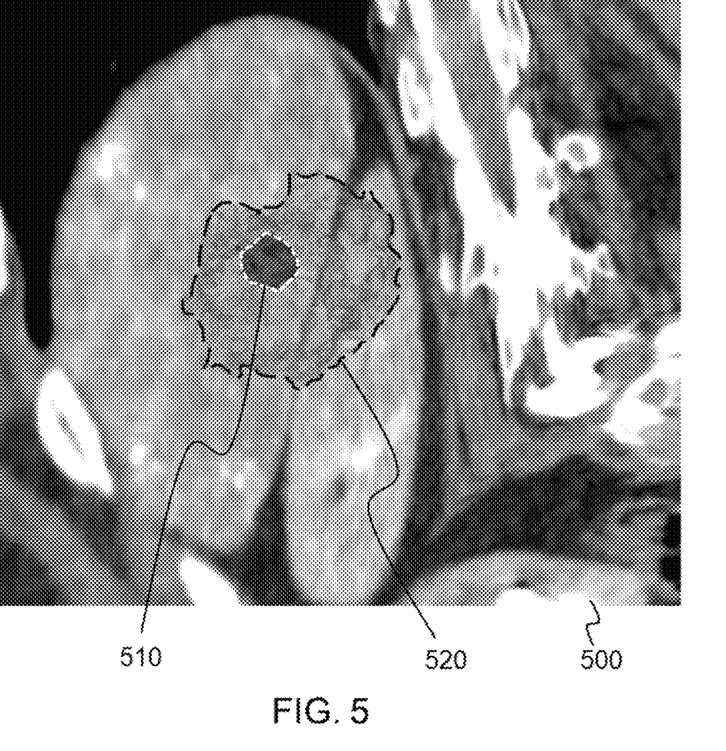
FIG. 5 is an example of a medical image in which a lesion and an ablation region are segmented automatically in a step of the method illustrated in FIG. 2.

This segmentation sub-step 243 is illustrated in FIG. 5, which shows a pre-operative medical image 500 in which automatic segmentation based on a deep learning method is performed in order to determine the three-dimensional location of the lesion 510 and of the ablation region 520. An equivalent result may be obtained using a third neural network separate from the two neural networks used previously.

An ablation margin is then determined between the segmentation of the lesion and the ablation mask that were established beforehand, in sub-step 244. The ablation margin corresponds to the minimum margin, that is to say to the minimum distance, noted between the segmentation of the lesion and the ablation mask. In other words, the ablation margin corresponds to the smallest distance calculated between a point of the lesion and a point of the ablation region, and is calculated for all points of the lesion.

Determining the ablation margins makes it possible to ensure that the ablation region actually covers the lesion.

Figure 6:
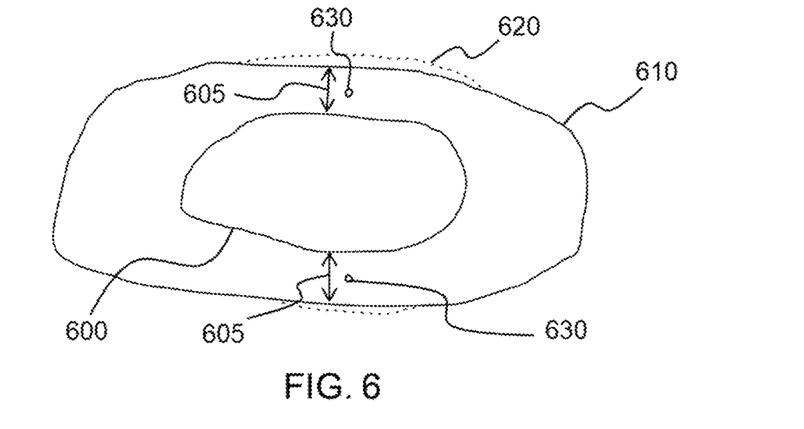
FIG. 6 illustrates an example of additional ablation, as possibly proposed by the method illustrated in FIG. 2.

FIG. 6 illustrates an example of additional ablation following an ablation treatment on a lesion 600 with risk of recurrence. The post-treatment evaluation method 200 has identified regions in which the ablation margins 605 were insufficient between the lesion 600 and the ablation region 610, and has generated an additional ablation mask 620. It should be emphasized that the additional ablation mask 620 is generated while attempting to limit the ablation area as far as possible. Target points 630 to be reached by an ablation needle may then furthermore be defined in the mask 620.

A prediction of the position of the recurrence may furthermore be evaluated in sub-step 245 by comparing the calculated ablation margin with reference values of the ablation margins that are associated with a recurrence status and stored in a database. For example, the risk of recurrence is considered to be low, or even zero, when the ablation margins are greater than or equal to 5 mm.

In addition or as an alternative, predictors of the risk of recurrence other than the ablation margins may be used. The position of the recurrence may be estimated by weighting all or some of these various predictors. By way of example, the predictors of the risk of recurrence may be:

a distance between the surface of the lesion, or part of the surface of the lesion, and the ablation region;
a distance between the centers of mass of the lesion and the centers of mass of the ablation region;

a distance between the surface of the lesion, or part of the surface of the lesion and the ablation region and the distance between the centers of mass of the lesion and the centers of mass of the ablation region, taking into account the proximity of the capsule of the anatomy of interest, in particular in the case of subcapsular lesions;
a regularity of the edges of the ablation region with respect to the surrounding healthy tissue;
a sharpness of the edges of the ablation region with respect to the surrounding healthy tissue;
a ratio between the volume of the lesion and the volume of the ablation region;
a position of the lesion in the anatomy of interest.

The reference value of the center of mass depends on the ablation margins. If the ablation margins are equal to 10 mm and the reference value of the ablation margins is 5 mm, the distance between the centers of mass of the lesion and the centers of mass of the ablation region should be less than or equal to 5 mm.

The method 200 may also comprise a step 250 of planning a trajectory to be followed by the medical instrument 120 associated either with the ablation mask or with the additional ablation mask, in order to guide the operator when handling the medical instrument 120 in a step 260 of guiding the medical instrument 120 along the planned trajectory.

One example of a planning method is described in French patent application No. 1914780 entitled "*Méthode de planification automatique d'une trajectoire pour une intervention médicale*" [*Method for automatically planning a trajectory for a medical intervention*].

It should be emphasized that the guidance, in the present non-limiting example of the invention, is visual, involving displaying the planned trajectory and/or a guidance indication on the screen 155 of the headset 150.

As an alternative, the medical instrument 120 may be guided by way of a navigation system providing position and orientation information for the medical instrument 120. This may involve mechanical guidance using a robotic device coupled to such a navigation system.

It should be emphasized that steps 230 to 260 may be repeated until the risk of recurrence is zero or almost zero, or until the ablation margins are sufficient.

The invention claimed is:

1. A method for the post-treatment evaluation of an ablation of part of an anatomy of interest of an individual, the anatomy of interest comprising at least one lesion, the ablated part of the anatomy of interest being called an ablation region, the post-treatment evaluation method comprising steps of:

acquiring a post-operative medical image of the anatomy of interest of the individual, comprising all or part of the ablation region;

readjusting the post-operative medical image and a pre-operative medical image of the anatomy of interest of the individual, the readjusted pre-operative medical image and the readjusted post-operative medical image forming a pair of medical images of the anatomy of interest of the individual; and evaluating a risk of recurrence of the lesion of the anatomy of interest of the individual using a neural network-based machine learning method, analyzing the pair of medical images of the anatomy of interest of the individual, said machine learning method being trained beforehand in a training phase on a database containing a plurality of pairs of medical images of an identical anatomy of interest of a set of patients, each pair of medical images in the database being associated with a recurrence status of a lesion of the anatomy of interest of said patient.

2. The post-treatment evaluation method of claim 1, wherein the risk of recurrence is evaluated at a predetermined date following the treatment, each pair of medical images in the database also being associated with a date of recurrence when the recurrence status is positive.

3. The post-treatment evaluation method of claim 1, wherein all or some of the pairs of images in the database are cropped, after readjustment, around an ablation region contained in the post-operative image of all or some of the pairs of training images, the images being cropped within a common frame of predetermined size, the set of centers of the ablation region in the cropped pairs of images forming a constellation of distinct points within the common frame.

4. The post-treatment evaluation method of claim 3, wherein, for all of the previously cropped pairs of medical images in the database, the part of the body of the individual contained in the image is divided into a plurality of elementary units of a single size, the number of elementary units being split into two almost equal portions between the part of the human body delimited by the ablation region and the rest of the part of the body of the individual contained in the image.

5. The post-treatment evaluation method of claim 1, wherein the database of pairs of medical images contains at least one pair of images without an ablation region.

6. The post-treatment evaluation method of claim 1, further comprising a step of determining an additional ablation mask when the risk of recurrence is greater than a predetermined threshold value.

7. The post-treatment evaluation method of claim 6, wherein the step of determining an additional ablation mask comprises a sub-step of detecting the ablation region in the post-operative image of the anatomy of interest of the individual.

8. The post-treatment evaluation method of claim 6, wherein the step of determining an additional ablation mask comprises a sub-step of segmenting the ablation region in the post-operative image of the anatomy of interest of the individual.

9. The post-treatment evaluation method of claim 6, wherein the step of determining an additional ablation mask comprises a sub-step of detecting the lesion in the pre-operative image of the anatomy of interest of the individual.

10. The post-treatment evaluation method of claim 6, wherein the step of determining an additional ablation mask comprises a sub-step of segmenting the lesion in the pre-operative image of the anatomy of interest of the individual.

11. The post-treatment evaluation method of claim 6, wherein the step of determining an additional ablation mask comprises a sub-step of determining the position of the recurrence as a function of at least one of the following risk predictors:
an ablation margin between the ablation region and the lesion,
a distance between a center of mass of the lesion and a center of mass of the ablation region,
the regularity and sharpness of the edges of the ablation region with respect to the surrounding healthy tissue,
the ratio between the volume of the lesion and the volume of the ablation region, and/or
a position of the lesion with respect to the center of the anatomy of interest.

12. The post-treatment evaluation method of claim 1, wherein the medical images are three-dimensional images.

13. The post-treatment evaluation method of claim 1, wherein each pre-operative image is acquired using a first image acquisition technique and each post-operative image is acquired using a second image acquisition technique, the first technique and the second technique being identical or different.

14. An electronic device (150) comprising a processor and a computer memory storing instructions of a post-treatment evaluation method of claim 1.

15. The electronic device of claim 14, wherein the electronic device is a control device, a navigation system, a robotic device or an augmented reality device.

* * * * *